(12) United States Patent
Cortelazzo

(10) Patent No.: US 7,297,550 B2
(45) Date of Patent: Nov. 20, 2007

(54) DISPOSABLE SUPPORT FOR CONTAINERS FOR TREATING BIOLOGICAL SAMPLES IN CYTOCENTRIFUGES

(75) Inventor: Lorenzo Cortelazzo, Padua (IT)

(73) Assignee: Kaltek S.R.L., Padua (IT)

( * ) Notice: Subject to any disclaimer, the term of this patent is extended or adjusted under 35 U.S.C. 154(b) by 54 days.

(21) Appl. No.: 10/600,461

(22) Filed: Jun. 23, 2003

(65) Prior Publication Data

US 2004/0007650 A1    Jan. 15, 2004

(30) Foreign Application Priority Data

Jul. 12, 2002   (IT) .......................... PD20020054 U

(51) Int. Cl.
  *G01N 1/18* (2006.01)
(52) U.S. Cl. .................... 436/177; 422/99; 422/100; 422/101; 422/102; 210/512.1; 220/501
(58) Field of Classification Search ................. 436/45, 436/177; 422/99–102; 210/512.1; 220/501
See application file for complete search history.

(56) References Cited

U.S. PATENT DOCUMENTS 4,209,923 A  * 7/1980  Wendt ........................ 40/710

4,391,710 A  7/1983  Gordon
4,853,188 A  8/1989  Toya
5,392,913 A  * 2/1995  Merrick ...................... 206/454
5,589,400 A  * 12/1996  Hayes ........................ 436/177

FOREIGN PATENT DOCUMENTS

EP  0 880 021   11/1998
GB  2 243 448   10/1991

* cited by examiner

*Primary Examiner*—Jill Warden
*Assistant Examiner*—Jyoti Nagpaul
(74) *Attorney, Agent, or Firm*—Modiano & Associati; Albert Josif; Daniel J. O'Byrne

(57) ABSTRACT

A disposable support for containers for treating biological samples in cytocentrifuges, that comprise a vertical flat supporting base with a protruding wall that supports at least one funnel connected in a lower region to a corresponding horizontal connection channel, the support being composed of a single element made of molded plastic material, and comprising a flat supporting body with protruding edges for accommodating, in succession, a slide, a filtering card and the container base, clamps for retaining the slide, the filtering card and the base container, and a transverse pivot for fixing the support to a cytocentrifuge.

7 Claims, 2 Drawing Sheets

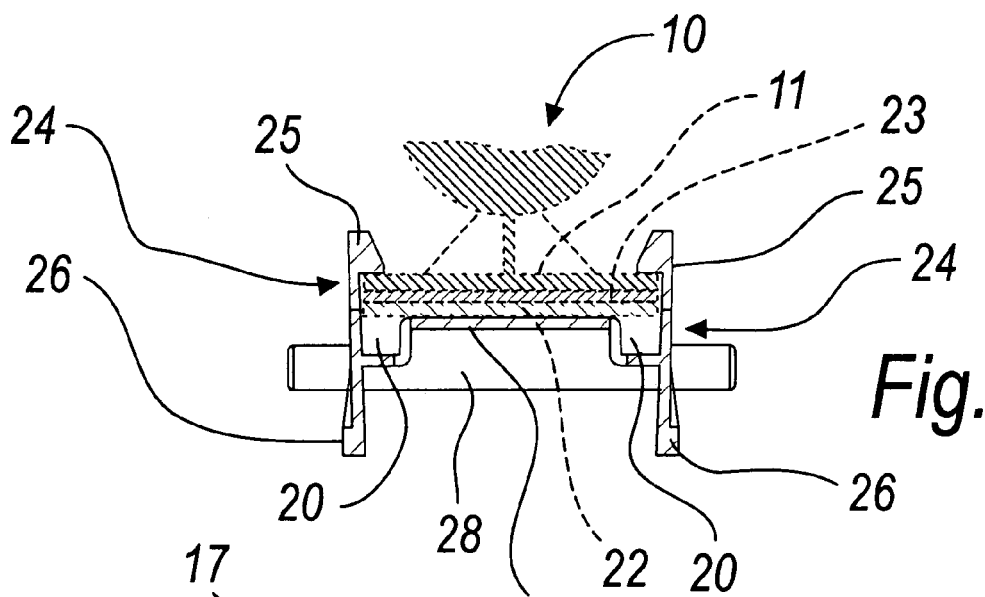
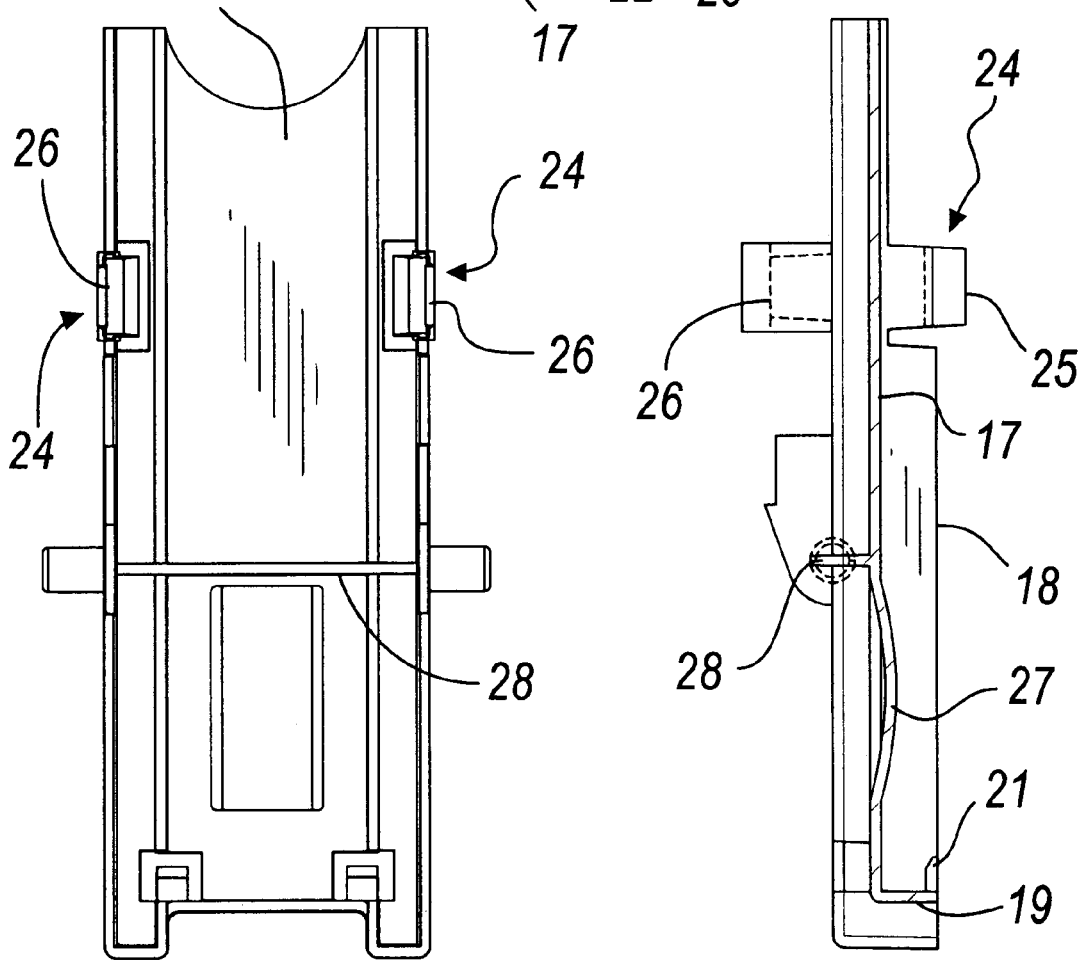
Fig. 3
Fig. 4
Fig. 5

DISPOSABLE SUPPORT FOR CONTAINERS FOR TREATING BIOLOGICAL SAMPLES IN CYTOCENTRIFUGES

BACKGROUND OF THE INVENTION

The present invention relates to a disposable support for containers for treating biological samples in cytocentrifuges.

Containers commonly known as cuvettes are already known which are constituted by a vertical flat resting base from which a wall protrudes at right angles, said wall supporting one or two funnels that are connected, in a lower region, to corresponding horizontal connection channels.

Such containers are used to treat biological samples by way of the cytocentrifugation technique.

To do so, the containers are rested, with a filtering card interposed, on a microscope slide and the assembly is reversibly fixed inside a cytocentrifuge.

For this purpose, the cytocentrifuge is provided with supports, each of which is currently constituted by a contoured steel element that forms a flat supporting body with raised edges in order to accommodate in succession the slide, the filtering card, and the base of the container, which are fixed thereto by means of a spring-loaded device constituted by a metal wire shaped like an inverted letter U, which is articulated with its lower ends to the flat body and can be rotated so as to be arranged substantially parallel to it and engage suitable tabs that protrude from the edges.

On the opposite side with respect to the engagement means, the body has a transverse pivot for fixing to the cytocentrifuge.

Cuvette supports are therefore an integral part of the centrifugation machine, and since they are the elements that make direct contact with the containers the supports must be very well cleaned for each individual test to be conducted.

This naturally causes problems in terms of the time required for cleaning and does not provide absolute certainty that the cleaning is perfect.

SUMMARY OF THE INVENTION

The aim of the present invention is to provide a support for containers for treating biological samples in cytocentrifuges that is of the disposable type and therefore can be used in combination with cuvettes and in the same manner as the cuvettes.

Within this aim, an object of the invention is to provide a support that can be sold by the manufacturer in combination with a slide, a filtering card and a cuvette as a disposable kit to be used in cytocentrifuges.

Another object is to provide a support that is structurally simple and has a low cost.

Another object is to provide a support that can be obtained in a finished condition with a small number of manufacturing operations.

This aim and these and other objects that will become better apparent hereinafter are achieved by a disposable support for containers for treating biological samples in cytocentrifuges, each one of the containers comprising a vertical flat supporting base from which a wall protrudes at right angles, said wall supporting at least one funnel that is connected in a lower region to a corresponding horizontal connection channel, said support being characterized in that it comprises, in a single element made of molded plastic material, a flat supporting body with protruding edges in order to accommodate in succession a slide, a filtering card and said base of said container for the treatment of biological samples, said protruding edges integrating clamp means for retaining the slide, the filtering card and the container, said body integrating a transverse pivot for fixing the support to a cytocentrifuge.

Advantageously, an elastic means for recovering any play is integrated in the body in the region of contact with the slide.

BRIEF DESCRIPTION OF THE DRAWINGS

Further characteristics and advantages of the invention will become better apparent from the following detailed description of an embodiment thereof, illustrated by way of non-limitative example in the accompanying drawings, wherein:

FIG. 3 is a transverse sectional view of the support of FIG. 1;

FIG. 4 is a rear view of the support of FIG. 1;

FIG. 5 is a longitudinal sectional view of the support of FIG. 1.

DESCRIPTION OF THE PREFERRED EMBODIMENTS

Figure 1:
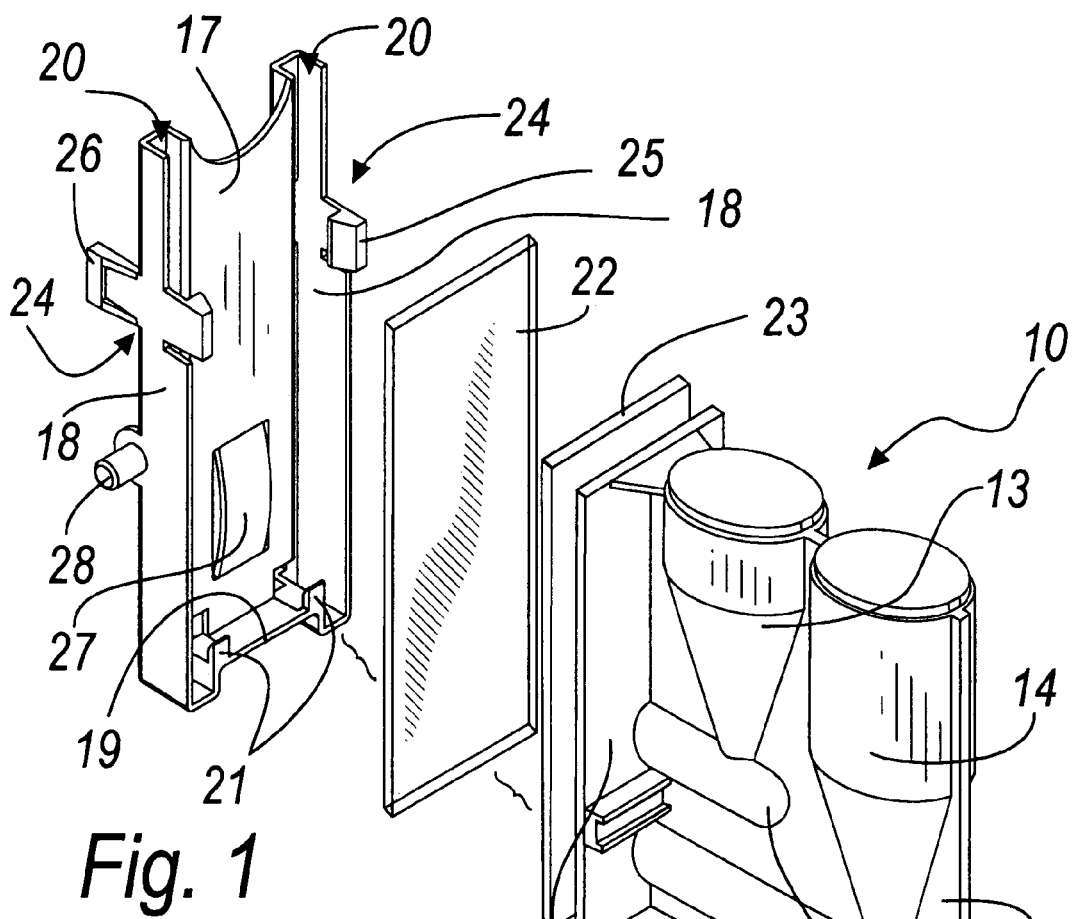
FIG. 1 is an exploded view of a disposable support according to the invention and of the components that must be associated therewith, i.e., the slide, the filter and the container for treating biological samples.
Figure 2:
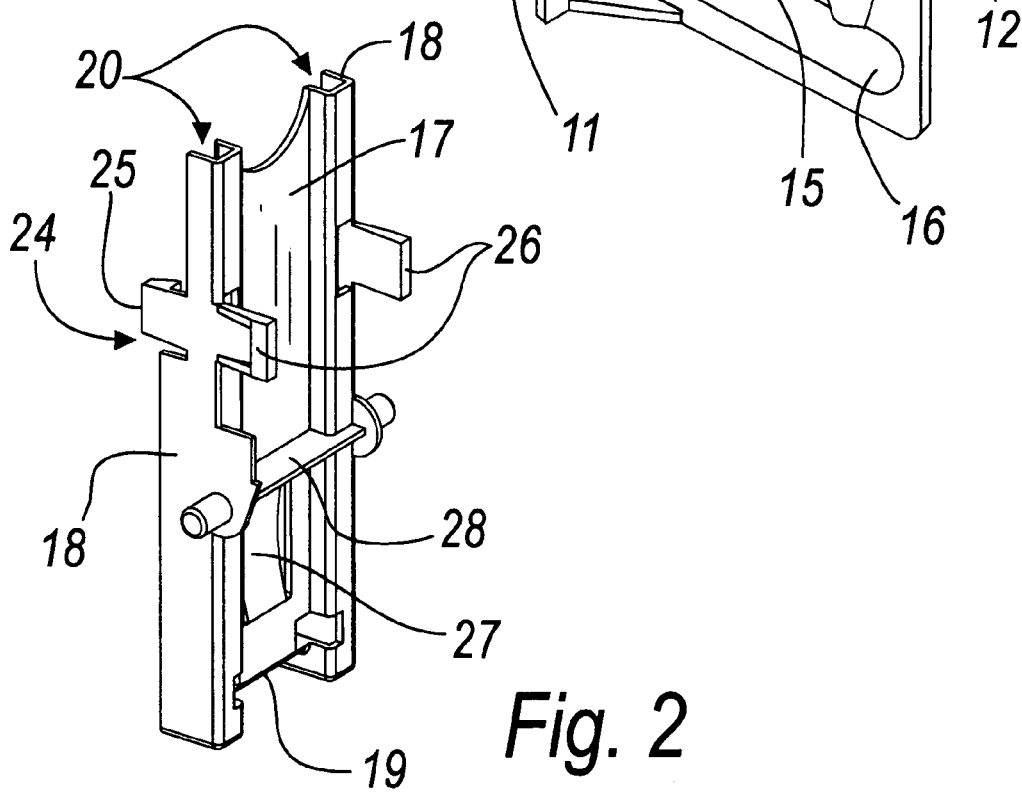
FIG. 2 is a rear perspective view of the support of FIG. 1.

With reference to the figures, a container for treating biological samples in cytocentrifuges is generally designated by the reference numeral 10 and comprises, in a single element made of molded plastic material, a vertical flat supporting base 11 from which a wall 12 protrudes at right angle, said wall supporting in this case two funnels, designated by the reference numerals 13 and 14 respectively, each funnel being connected in a lower region to a corresponding horizontal connection channel 15 and 16.

A disposable support according to the invention for containers 10 comprises, in a single monolithic molded plastic element, a flat supporting body 17 with protruding longitudinal edges 18 and a lower edge 19 that also protrudes.

The connection between the longitudinal edges 18 and the body 17 is provided by forming respective longitudinal channels 20, while the lower edge 19 has, in respective regions located substantially at the ends, two small perpendicular containment tabs 21.

The body 17 with the edges 18 and 19 is adapted to accommodate in succession a slide 22, a filtering card 23, and the base 11 of the container 10, as shown in particular in FIGS. 1 and 3.

These elements are retained in a lower region by the tabs 21 and in an upper region by clamp means 24, which are integrated with the longitudinal edges 18.

The clamp means 24 are constituted by two mutually opposite hook-shaped tabs 25, which are sized so as to retain between their ends and the body 17 the elements cited above in succession.

The tabs 25 are extended, in the rear part of said body, with respective levers 26.

In practice, by moving the levers 26 mutually closer with one's fingers, an elastic flexing motion is produced which moves apart the ends of the tabs 25, allowing to insert the slide 22, the filtering card 23 and the base 11.

The fixing engagement of the assembly is obtained by releasing the levers 26.

Also according to the invention, the flat body 17 integrates an elastic means 27 for taking up any plays, which is constituted in practice by a longitudinal bridge-like element that is designated by the same reference numeral and protrudes from the part that supports the slide 22 and in practice constitutes a sort of leaf spring.

On the opposite side of the region where the slide 22 rests, the flat body 17 integrates a transverse pivot 28 for fixing to a cytocentrifuge, which is not shown in the figures.

In practice it has been found that the intended aim and objects of the present invention have been achieved.

The support can in fact be obtained with a single molding operation, for example by injection-molding plastic material, and is therefore extremely cheap and therefore usable as a disposable item.

This allows to market complete single-use kits constituted by a support, a slide, filter paper and a container of biological samples.

In practice, the materials employed, so long as they are compatible with the contingent use, as well as the dimensions, may be any according to requirements.

The disclosures in Italian Utility Model Application No. PD2002U000054 from which this application claims priority are incorporated herein by reference.

What is claimed is:

1. A disposable, single-use holder support for a sample container assembly for treating biological samples in cytocentrifuges, the sample container assembly being a unitary disposable plastic body comprising, as arranged in a mounting position in a cytocentrifuge, a vertical flat supporting base for supporting by insertion thereof in said holder support the sample container assembly in an upright position upon mounting of the sample container assembly in the cytocentrifuge, a wall protruding at right angles from said supporting base, at least one funnel supported by the wall and provided in a lower region thereof with a corresponding horizontal connection channel extending along said wall and away from and perpendicularly to said supporting base between the lower region of the funnel and the supporting base, a slide, and a filtering card, the disposable holder support being formed from a single element made of molded plastic material that is suitable to be detachably connected with the sample container assembly and comprising:

a flat supporting body provided with edges that protrude therefrom so as to form a seat adapted to accommodate said slide, filtering card and supporting base of the sample container assembly; clamp means provided at said edges for detachably accommodating and retaining, in succession, the slide, the filtering card and the supporting base of the sample container; and a transverse pivot protruding from said supporting body for fixing the support to a cytocentrifuge, said supporting body, clamp means and transverse pivot of the holder support forming a monolithic structure of plastic material.

2. The support of claim 1, further comprising elastic means for taking up, upon accommodation of the slide, filtering card and container base, mounting plays, said elastic means being made monolithic with said supporting body in a region where the slide rests.

3. The support of claim 1, wherein said protruding edges comprise longitudinal edges and a protruding lower edge.

4. The support of claim 3, comprising respective longitudinal channels formed at said longitudinal edges that connect the longitudinal edges to said supporting body.

5. The support of claim 3, wherein said lower edge has at least one perpendicular containment tab.

6. The support of claim 1, wherein said clamp means are constituted by two mutually opposite hook-shaped tabs, which are sized so as to retain between ends thereof and said supporting body the slide, the filtering card and the supporting base of the container, said hook-shaped tabs comprising respective levers that extend towards a rear part of said supporting body.

7. The support of claim 2, wherein said elastic means for taking up the mounting plays is constituted by a longitudinal bridge element that protrudes from a part of the supporting base where said slide rests, said bridge element being shaped as a leaf spring.

* * * * *